United States Patent [19]

Bier et al.

[11] 4,406,886

[45] Sep. 27, 1983

[54] PURIFICATION OF ANTIHEMOPHILIA FACTOR VIII BY PRECIPITATION WITH ZINC IONS

[75] Inventors: Milan Bier, Tucson, Ariz.; Peter R. Foster, Edinburgh, Scotland

[73] Assignee: University Patents, Inc., Norwalk, Conn.

[21] Appl. No.: 458,128

[22] Filed: Jan. 14, 1983

[51] Int. Cl.$^3$ ............................................. A61K 35/14
[52] U.S. Cl. ................................................... 424/101
[58] Field of Search ........................................ 424/101

[56] References Cited

PUBLICATIONS

Simonetti et al.–Chem. Abst., vol. 72, (1970), p. 28805b.
Greencross–Chem. Abst., vol. 95, (1981), 30387k.

*Primary Examiner*—Sam Rosen
*Attorney, Agent, or Firm*—George M. Yahwak

[57] ABSTRACT

The present invention relates to the reduction of the fibrinogen concentration in cryoprecipitate fraction formed during the fractionation of blood. This zinc-mediated decrease of fibrinogen increases the ratio of Factor VIII to total protein content.

12 Claims, No Drawings

PURIFICATION OF ANTIHEMOPHILIA FACTOR VIII BY PRECIPITATION WITH ZINC IONS

The present invention relates to the fractionation of blood, and more specifically to the production and purification of blood factor VIII.

The economics of commercial plasma fractionation are primarily based on three products: antihemophilia factor VIII concentrate (AHF), serum albumin, and immunoglobulins. The present invention deals with improvements in the production of purified factor VIII concentrates. These are used for the treatment of accute bleeding episodes in patients suffering from classical hemophilia, i.e., patients having an inherited insufficiency of factor VIII in their blood.

The key to the present production of factor VIII is the cryoprecipitate, discovered by J. G. Pool and A. E. Shannon (Production of High Potency Concentrates of Antihemophilic Globulin in a Closed-bag System, *New England J. of Medicine*, 273:1443 (1965)). Pool and her co-workers found that if freshly frozen plasma is thawed at room temperature, all of the proteins in the plasma will go into solution. If, however, frozen plasma is thawed at low temperatures, for example temperatures below 8° C., some of the plasma proteins do not go into solution, but can be centrifuged off as the cryoprecipitate. Typically, this cryoprecipitate recovers about 40-60% of factor VIII activity present in the starting plasma. Thus, the conventional first step in commercial plasma fractionation is the collection of cryoprecipitate. The freshly frozen plasma is thawed under controlled temperature conditions, either in individual bags of plasma, as described by Pool and Shannon, or after pooling of the contents of the frozen bags. The supernatant after removal of cryoprecipitate may subsequently be processed for the recovery of immunoglobulins and serum albumin.

Since this original discovery of cryoprecipitate, there have been numerous studies to improve the yield of factor VIII, and to further purify it. For example, a minimal purification step is the treatment of cryoprecipitate with aluminum hydroxide gels. This eliminates some of the minor blood clotting factors, stabilizes the activity of factor VIII, and facilitates its subsequent sterile filtration. There are also several schemes for further purification, as disclosed in a number of United States Patents, for example, Nos. 3,652,530 to Johnson et al., 3,682,881 to Fekete et al., 3,973,002 to Hagan et al., 4,188,318 to Shanbrom, 4,203,891 to Rock, 4,210,580 and 4,278,594 to Amrani, 4,289,691 to Rock, and 4,297,344 to Schwinn et al. The number of these patents since the original work by Pool and her co-workers attest to the importance of the further purification of AHF, and the fact that the present methods are not quite satisfactory when applied on a commercial scale.

The major shortcoming of present technology is that it results in rather unacceptable losses of factor VIII activity. In addition, it has long been accepted that commercial preparations of factor VIII vary greatly in terms of anticoagulant activity, total protein content, and contamination by fibrinogen (cf., for example, J. P. Allain et al.: In vitro and in vivo Characterization of Factor VIII Preparations, *Vox Sang.*; 38:68, (1980)). Fibrinogen is one of the main protein contaminants in cryoprecipitate, and the ratio of fibrinogen to factor VIII varies among individual cryoprecipitate preparations (P. M. Ness et al.: Fibrinogen in Cryoprecipitate and its Relationship to Factor VIII (AHF) Levels, *Transfusion*, 20:93, (1980)). Thus, all presently known methods for the purification of factor VIII preparations involve, by necessity, the separation of factor VIII from fibrinogen. After purification, factor VIII concentrates are normally sterile filtered and freeze-dried, to be reconstituted with distilled water shortly before administration to the patient.

Cryoprecipitate also contains a variety of other biologically important proteins besides factor VIII and fibrinogen. Most of these other proteins are present in trace amounts, and cryoprecipitate is not usually considered as a source material for their isolation. In fact, factor VIII purification schemes usually aim only at the elimination, not the isolation, of these "impurities". An exception to this may be fibronectin, a high molecular weight glycoprotein (D. F. Mosher: Fibronectin, in "Progress in Hemostasis & Thrombosis", 5:111, (1980)). Fibronectin has multiple biological functions and is currently the object of a great amount of research. Thus, it can be expected that it may acquire clinical importance, and since it is found in concentrated form in cryoprecipitate, the latter may become an intermediate in its commercial preparation.

The principal objective of the present invention is the reduction of fibrinogen concentration in cryoprecipitate preparations, for the purpose of increasing the ratio of factor VIII to total protein content. The invention is based on my fortuitous observation that the addition of zinc ions to cryoprecipitate preparations causes a selective precipitation of a zinc-fibrinogen complex. The precipitation is quite rapid, and under optimal conditions, nearly instantaneous. It does not cause an activation of factor VIII, or an unacceptable loss of its activity, if an excess of zinc ion concentration is avoided. The precipitate settles rapidly and the suspension is easily clarified by centrifugation. The precipitate is often fibrous in character and can also be removed by winding it on a rod, as is frequently done with actual fibrin clots.

Zinc ions are added as concentrated solutions of zinc salts of weak acids, with rapid mixing to avoid excessive local concentrations. As factor VIII has a relatively narrow range of pH stability, being most stable in the neutral pH range (that is between pH 6 and pH 8), it is advantageous to use a source of zinc ions which will not cause significant change in pH. Examples of such salts are zinc acetate, zinc glycinate, or zinc diglycinate. Zinc chloride, to the contrary, will cause a significant decrease in pH and its use is not recommended for this application. Plasma is usually collected using citrate as anticoagulant, which is carried over into the cryoprecipitate, and the concentration of zinc ions required to cause a given precipitation is dependent on citrate concentration. The optimal range of zinc concentration for a given separation is rather narrow: at too low concentrations no precipitation occurs, while at too high concentrations an unacceptable loss of factor VIII is observed. Thus, the zinc should be added in incremental amounts, until the desired effect is obtained. Normally, this is until a permanent visibly heavy precipitate is obtained, thus establishing the minimum threshold volume of the zinc solution required for the precipitation of the zinc-protein complex; addition of the zinc solution is continued until the total volume added is 1-2.5 (preferably 1.1 to 2) times the threshold volume amount. Alternatively, the necessary zinc ion addition can be calculated from analytical data on the citrate content of the cryoprecipitate. In general, it is not practical to try to obtain complete precipitation of all fibrinogen, but an elimination of 50-75% can be readily achieved without an unacceptable loss of factor VIII. Thus, the objective of the present invention is a decrease of fibrinogen content, not its complete elimination.

The supernatant, after removal of the zinc-fibrinogen complex, is often seen to develop turbidity due to a slow secondary precipitation. This can be prevented and the supernatant stabilized by the addition of small quantities of citrate.

A secondary objective of the invention is the separation of fibronectin from factor VIII, for the purpose of its subsequent purification. In fact, as will be shown, a major proportion of fibronectin is found in the precipitated fraction, from where it can be isolated by any number of procedures, well described in the literature.

Zinc ions are quite non-toxic, are considered an essential mineral component of human diet, and are actually often prescribed for therapeutic purposes. Therefore, the small quantities of residual zinc remaining in the cryoprecipitate are physiologically acceptable. Alternatively, zinc may be eliminated or reduced by a variety of well known procedures, such as ion exchange using sodium-saturated cation exchange columns, diafiltration, electrodialysis, or precipitation of Factor VIII with polyethylene glycol (PEG).

The main virtue of the invention is the extreme simplicity and speed of the procedure. Thus, it is far more cost effective than many present day procedures which require more extensive or protracted manipulation of the cryoprecipitate. It is, therefore, eminently well suited for the commercial purification of these costly materials in limited supply.

Following the zinc precipitation, the clarified cryoprecipitate can be further processed in any desired manner for the preparation of the final commercial product. This processing may involve such conventional steps as adsorption on alumina gel and freeze-drying, or steps for protein concentration, such as ultra-or diafiltration. Of course, zinc precipitation can also be carried out any any appropriate point in a Factor VIII purification process, e.g. before or after Al (OH)$_3$ adsorption.

The following examples are given to further illustrate the procedure and advantages of the present invention:

EXAMPLE 1

This example illustrates the removal of fibrinogen from cryoprecipitate by the controlled addition of zinc ions. In addition, the differences in effects of calcium and zinc ions are shown. Factor VIII activities were determined using a one-stage assay method; total proteins by the biuret method; and fibrinogen by the method of Bang (*Scand. J. Clin. Lab. Invest.;* 9:205 (1957)).

Thirty ml aliquots of a batch of freshly prepared cryoprecipitate were used. A small-scale laboratory procedure was used for the preparation of cryoprecipitate, which was not rinsed to remove adherent plasma fluid. Thus, this cryoprecipitate preparation had significantly higher levels of citrate than found in commercial cryoprecipitate production. Precipitation was carried out at room temperature by the slow addition of a 500 mM zinc acetate solution, with good stirring. The addition of 0.6 ml of the zinc acetate solution caused no substantial precipitation of fibrinogen, while an additional increment of 0.2 ml. of the zinc solution caused massive precipitation, virtually completed within 3 min. Another aliquot was then treated with 1.0 ml of zinc solution and here the precipitation was immediate. The precipitate was removed and the supernatants assayed for factor VIII, total protein, and fibrinogen.

Because calcium ions are known to cause the clotting of fibrinogen through activation of the clotting factors present in cryoprecipitate, and as both, zinc and calcium, are divalent, it was deemed desirable to compare the observed effects of zinc addition with those obtainable by the addition of a 500 mM calcium chloride solution. The addition of 1 ml of the calcium solution to another 30 ml. aliquot of the cryoprecipitate causes no clotting within 6 min. An additional increment of 0.2 ml of the calcium solution caused clotting of the fibrinogen, the whole solution gelling. The fibrin clot was removed, and the extruded supernatant used for factor VIII, total protein and fibrinogen assays. This experiment was repeated with another aliquot, to which 1.4 ml of the calcium solution was added. A very solid, hard gel was obtained and treated as above.

The analytical data obtained from this example are shown in the following TABLE I.

TABLE I

COMPARISON OF THE EFFECTS OF ZINC AND CALCIUM IONS ON CRYOPRECIPITATE

| Reagent | Ion Concentr. (mM/L) | Factor VIII (U/ml) | Total Protein (Mg/ml) | Fibrinogen (mg/ml) |
|---|---|---|---|---|
| Cryoprecipitate | 0 | 7.2 | 22.7 | 13.1 |
| +0.8 ml zinc | 13.0 | 6.4 | 16.5 | 7.2 |
| +1.0 ml zinc | 16.1 | 4.2 | 11.3 | 1.8 |
| +1.2 ml calcium | 19.2 | 0.9 | 10.0 | N.D. |
| +1.4 ml calcium | 22.3 | 0.5 | 9.8 | N.D. |

N.D.: not detectable.

Some striking differences between the use of zinc and calcium were observed. With zinc, the reaction is near instantaneous, resulting in a fibrous precipitate, while with calcium there is an unavoidable incubation period, necessary for the activation of the clotting factors, and the reaction result in gelling of the whole fluid content. The tabulated data clearly show that the zinc precipitation causes a significant lowering of total protein and fibrinogen levels in the cryoprecipitate, while preserving in excess of 50% of factor VIII activity. The gelling which occurred by the addition of calcium ion caused a far greater loss of factor VIII activity. The most important difference in the properties of the precipitation is that the zinc-induced fibrinogen precipitate is soluble in a pH6 citrate buffer, while the calcium-clotted fibrin is insoluble.

EXAMPLE 2

The previous experiment reported factor VIII activities obtained using the one-stage assay method. To avoid any question relating to the reliability of this assay in presence of zinc ions, this experiment was performed in which five different assay methods (according to Prowse et al. (*Thromb. Haem.* 46:597 (1981)) were used to assess the effects of zinc precipitation. These methods were dependent on factor VIII coagulant activity, as well as its antigenic characteristics:

Factor VIII Coagulant Activity (FVIII:C)
  1-stage assay (repeated in two independent laboratories),
  2-stage assay.
Factor VIII Related Antigen (FVIIIR:Ag)
  Non-reduced assay, Reduced assay.
Factor VIII Coagulant Antigen (FVIIIC:Ag)
The activity data on supernatants obtained after zinc precipitation are summarized in TABLES II and III.

lower zinc ion concentration necessary with the large scale prepared cryoprecipitate. This is due to the fact that its citrate level (about 2 mM) is about an order of magnitude lower than that in the laboratory-produced cryoprecipitate.

TABLE II

EFFECT OF ZINC PRECIPITATION ON CRYOPRECIPITATE
PERCENT ACTIVITY OR CONCENTRATION
RECOVERED IN SUPERNATANT
(MEAN OF n EXPERIMENTS)

| ZINC (mM) | TIME (min) | FVIII:C 1 stage (a) | FVIII:C 1 stage (b) | TOTAL PROTEIN | FIBRINOGEN |
|---|---|---|---|---|---|
| 0.50 | 20 | 105 (n = 5) | 89 (n = 3) | 79 (n = 5) | 63 (n = 3) |
|  | 40 | 105 (n = 5) | 85 (n = 2) | 79 (n = 5) | 52 (n = 5) |
|  | 60 | 100 (n = 4) | 106 (n = 1) | 81 (n = 4) | 61 (n = 4) |
| 0.75 | 20 | 111 (n = 4) | 88 (n = 2) | 68 (n = 4) | 15 (n = 3) |
|  | 40 | 112 (n = 4) | 83 (n = 2) | 68 (n = 4) | 32 (n = 3) |
|  | 60 | 117 (n = 3) | 106 (n = 1) | 63 (n = 3) | 30 (n = 2) |
| 1.00 | 20 | 111 (n = 7) | 87 (n = 4) | 57 (n = 7) | 14 (n = 5) |
|  | 40 | 103 (n = 5) | 85 (n = 2) | 58 (n = 5) | 12 (n = 3) |
|  | 60 | 113 (n = 3) | 101 (n = 1) | 56 (n = 3) | 22 (n = 3) |
| 1.50 | 20 | 90 (n = 4) | 80 (n = 2) | 46 (n = 4) | 1.5 (n = 4) |
|  | 40 | 93 (n = 4) | 75 (n = 2) | 45 (n = 4) | 1.0 (n = 4) |
|  | 60 | 103 (n = 3) | 73 (n = 1) | 43 (n = 3) | 1.6 (n = 3) |

TABLE III

ZINC PRECIPITATION - COMPARISON OF ASSAY METHODS
PERCENT OF ACTIVITY RECOVERED IN SUPERNATANT
(MEAN OF n EXPERIMENTS)

| ZINC (mM) | TIME (min) | FVIII:C 2 Stage | FVIIIR:Ag Non Reduced | FVIIIR:Ag Reduced | FVIIIC:Ag |
|---|---|---|---|---|---|
| 0.50 | 20 | 97 (n = 3) | 89 (n = 3) | 88 (n = 3) | 105 (n = 4) |
|  | 40 | 97 (n = 2) | 101 (n = 2) | 88 (n = 3) | 122 (n = 4) |
|  | 60 | 102 (n = 1) | 85 (n = 1) | 99 (n = 2) | 120 (n = 3) |
| 0.75 | 20 | 92 (n = 2) | 92 (n = 2) | 88 (n = 3) | 97 (n = 4) |
|  | 40 | 88 (n = 2) | 108 (n = 2) | 89 (n = 3) | 113 (n = 4) |
|  | 60 | 104 (n = 1) | 69 (n = 1) | 88 (n = 2) | 120 (n = 3) |
| 1.00 | 20 | 79 (n = 4) | 118 (n = 2) | 84 (n = 4) | 98 (n = 5) |
|  | 40 | 81 (n = 2) | 111 (n = 2) | 88 (n = 3) | 103 (n = 4) |
|  | 60 | 105 (n = 1) | 76 (n = 1) | 99 (n = 2) | 123 (n = 3) |
| 1.50 | 20 | 66 (n = 2) | 106 (n = 2) | 72 (n = 3) | 87 (n = 4) |
|  | 40 | 66 (n = 2) | 94 (n = 2) | 79 (n = 3) | 90 (n = 4) |
|  | 60 | 60 (n = 1) | 66 (n = 1) | 90 (n = 2) | 112 (n = 3) |

The FVIII:C one-stage assays were carried out in two laboratories (a and b), and both data are included in Table II. All experiments (the number of experiments is indicated in parenthesis) were conducted on aliquots of cryoprecipitate derived from a large scale manufacture of Factor VIII from fresh-frozen plasma. The data are reported as percent activity (or concentration) with respect to the starting cryoprecipitate.

Table II reproduces the data on factor VIII activity, as measured by the one-stage method, as well as total protein and fibrinogen. Table III shows the corresponding factor VIII activities as determined by other methods. The data obtained with five different assays are in essential agreement and confirm those obtained in Example 1. There is one significant difference: the much

EXAMPLE 3

Heparin is well known to exert a stabilizing influence on factor VIII and is often added to cryoprecipitate in the course of its purification. For this reason, all data reported in Example 2 were repeated, the precipitation being carried out in the presence of 1 unit/ml of heparin in the cryoprecipitate. The data were organized in an identical manner as in Example 2, and the results are reproduced in TABLES IV and V, to be compared directly with TABLES II and III. These data are shown to document that the zinc ion precipitation can be carried out in presence or absence of heparin, with essentially similar results.

TABLE IV

EFFECT OF ZINC PRECIPITATION IN PRESENCE OF HEPARIN+
PERCENT ACTIVITY OR CONCENTRATION
RECOVERED IN SUPERNATANT
(MEAN OF n EXPERIMENTS)

| ZINC (mM) | TIME (min) | FVIIIC (a) | FVIIIC (b) | TOTAL PROTEIN | FIBRINOGEN |
|---|---|---|---|---|---|
| 0.50 | 20 | 106 (n = 2) | 88 (n = 2) | 77 (n = 2) | 75 (n = 1) |
|  | 40 | 111 (n = 2) | 92 (n = 1) | 81 (n = 2) | 81 (n = 1) |
|  | 60 | 87 (n = 1) | 92 (n = 1) | 73 (n = 1) | * |
| 0.75 | 20 | 115 (n = 2) | 129 (n = 2) | 69 (n = 2) | 63 (n = 1) |

TABLE IV-continued

EFFECT OF ZINC PRECIPITATION IN PRESENCE OF HEPARIN+
PERCENT ACTIVITY OR CONCENTRATION
RECOVERED IN SUPERNATANT
(MEAN OF n EXPERIMENTS)

| ZINC (mM) | TIME (min) | FVIIIC (a) | FVIIIC (b) | TOTAL PROTEIN | FIBRINOGEN |
|---|---|---|---|---|---|
|  | 40 | 98 (n = 2) | 91 (n = 2) | 71 (n = 2) | * |
|  | 60 | 104 (n = 1) | 81 (n = 1) | 66 (n = 1) | * |
| 1.00 | 20 | 111 (n = 2) | 119 (n = 2) | 52 (n = 2) | * |
|  | 40 | 128 (n = 2) | 80 (n = 2) | 60 (n = 2) | * |
|  | 60 | 150 (n = 1) | 86 (n = 1) |  | * |
| 1.50 | 20 | 91 (n = 2) | 87 (n = 2) | 50 (n = 2) | * |
|  | 40 | 97 (n = 2) | 65 (n = 2) | 49 (n = 2) | * |
|  | 60 | 103 (n = 1) | 79 (n = 1) | 58 (n = 1) | * |

+One unit of heparin per ml of cryoprecipitate.
*The clot was too fragile for a good assay.

TABLE V

ZINC PRECIPITATION COMPARISON OF ASSAY METHODS+
PERCENT ACTIVITY RECOVERED IN SUPERNATANT
(MEAN OF n EXPERIMENTS)

| ZINC (mM) | TIME (min) | FVIII:C 2 Stage | FVIIIR:Ag Non Reduced | FVIIIR:Ag Reduced | FVIIIC:Ag |
|---|---|---|---|---|---|
| 0.50 | 20 | 91 (n = 1) | 118 (n = 2) | 82 (n = 2) | 121 (n = 2) |
|  | 40 | 82 (n = 1) | 104 (n = 2) | 89 (n = 2) | 115 (n = 2) |
|  | 60 | 82 (n = 1) | 90 (n = 1) | 93 (n = 1) | 109 (n = 1) |
| 0.75 | 20 | 80 (n = 1) | 123 (n = 2) | 98 (n = 2) | 114 (n = 2) |
|  | 40 | 80 (n = 1) | 108 (n = 2) | 94 (n = 2) | 117 (n = 2) |
|  | 60 | 93 (n = 1) | 115 (n = 1) | 98 (n = 1) | 97 (n = 1) |
| 1.00 | 20 | 86 (n = 2) | 113 (n = 2) | 90 (n = 2) | 107 (n = 2) |
|  | 40 | 84 (n = 2) | 102 (n = 2) | 80 (n = 2) | 121 (n = 2) |
|  | 60 | 76 (n = 1) | 115 (n = 1) | 106 (n = 1) | 115 (n = 1) |
| 1.50 | 20 | 73 (n = 1) | 105 (n = 2) | 83 (n = 2) | 98 (n = 2) |
|  | 40 | 86 (n = 1) | 103 (n = 2) | 77 (n = 2) | 90 (n = 2) |
|  | 60 | 65 (n = 1) | 91 (n = 1) | 87 (n = 1) | 91 (n = 1) |

+ Precipitation was carried out in presence of 1 unit/ml of heparin in the cryoprecipitate.

EXAMPLE 4

The stability of factor VIII preparations is decreased by the presence of other coagulation factors. Precipitation with zinc ions has a variable effect on these factors, as shown in TABLE VI. Factor II and VII are decreased the most, factor IX the least. Determinations of factor IX in presence of heparin have indicated greater decrease in its activity, but the data may have been vitiated by the presence of heparin.

EXAMPLE 5

This experiment was designed to show the fate of fibronectin in zinc precipitation. In absence of heparin, 1 mM zinc concentration causes only 25% of fibronectin to precipitate, but in presence of heparin, this precipitation is increased to 40%. These data are comparable to those reported previously for the precipitation of fibronectin from cryoprecipitate, which range from 25% precipitation with 3.5% polytheylene glycol (PEG) or the 50% precipitation obtained by the cold-

TABLE VI

EFFECT OF ZINC PRECIPITATION ON OTHER CLOTTING FACTORS
PERCENT ACTIVITY RECOVERED IN SUPERNATANT
(MEAN OF n EXPERIMENTS)

| ZINC (mM) | TIME (min) | FIX* | FII** | FVII** | FX** |
|---|---|---|---|---|---|
| 0.50 | 20 | 122 (n = 1) | 54 (n = 1) | 60 (n = 1) | 105 (n = 1) |
|  | 40 | 118 (n = 1) | 51 (n = 1) | 58 (n = 1) | 131 (n = 1) |
|  | 60 | 101 (n = 1) |  | 60 (n = 1) | 118 (n = 1) |
| 0.75 | 20 | 117 (n = 1) | 28 (n = 1) | 49 (n = 1) | 81 (n = 1) |
|  | 40 | 99 (n = 1) | 21 (n = 1) | 51 (n = 1) | 81 (n = 1) |
|  | 60 | 121 (n = 1) | 21 (n = 1) | 54 (n = 1) | 94 (n = 1) |
| 1.00 | 20 | 102 (n = 2) | 14 (n = 1) | 33 (n = 1) | 83 (n = 1) |
|  | 40 | 89 (n = 1) | 14 (n = 1) | 33 (n = 1) | 69 (n = 1) |
|  | 60 | 102 (n = 1) | 14 (n = 1) | 33 (n = 1) | 69 (n = 1) |
| 1.50 | 20 | 94 (n = 1) | 8 (n = 1) | 35 (n = 1) | 59 (n = 1) |
|  | 40 | 118 (n = 1) | 4 (n = 1) | 35 (n = 1) | 59 (n = 1) |
|  | 60 | 85 (n = 1) | 4 (n = 1) | 18 (n = 1) | 59 (n = 1) |

*Factor IX assay refers to zinc precipitation in absence of heparin.
**All other factors were assayed on supernatants of zinc precipitation carried out in the presence of 1 unit/ml of heparin.

acid method. Thus, zinc ion precipitation may constitute an alternate method for the isolation of fibronectin.

EXAMPLE 6

Our initial data showed about 20% of the fibronectin was precipitated at 1.0 mM zinc, and 40–50% with 1 u/ml heparin added at pH 7.0 and room temperature; to improve this, changes in pH and temperature were studied. The results of these studies are reported in Table VII which shows the effects of pH and temperature of supernatant following precipitation with zinc (1.0 mM) and in the presence of heparin (1.0 u/ml).

TABLE VII

PRECIPITATION OF FIBRONECTIN BY ZINC/HEPARIN

| CONDITIONS | | MEAN % VALUE IN SUPERNATANT* | |
|---|---|---|---|
| pH | TEMP. °C. | % FIBRONECTIN | % FACTOR VIII |
| 7.0 | 22 | 49 | 96 |
| 6.8 | 22 | 39 | 96 |
| 6.8 | 15 | 49 | 94 |
| 6.8 | 10 | 29 | 89 |
| 6.6 | 22 | 33 | 98 |
| 6.6 | 15 | 47 | 83 |
| 6.6 | 10 | 47 | 81 |

*Cryoprecipitate extract = 100%

Thus, while we have illustrated and described the preferred embodiment of our invention, it is to be understood that this invention is capable of variation and modification, and we therefore do not wish to be limited to the precise terms set forth, but desire to avail ourselves of such changes and alternations which may be made for adapting the invention to various usages and conditions. Accordingly, such changes and alternations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which it is most nearly connected, to make and use the same.

We claim:

1. The method for the preparation and purification of Factor VIII concentrates which comprises the addition of zinc ions in solution to a cryoprecipitate derived from blood plasma and comprising Factor VIII, fibrinogen, and fibronectin, said zinc ions being added in an amount sufficient to initate a precipitation of fibrinogen and fibronectin rich zinc-protein complexes from said cryoprecipitate.

2. The method of claim 1 in which said addition is conducted in a neutral pH range.

3. The method of claim 1 wherein said zinc ions are introduced into the cryoprecipitate as zinc salts of weak acids.

4. The method of claim 3 wherein the zinc salts are selected from the group of zinc acetate, zinc glycinate, and zinc diglycinate.

5. The method of claim 1 which further comprises mixing of the cryoprecipitate at the time of addition.

6. The method of claim 1 wherein the total volume of the zinc ions solutions added is 1 to 2.5 times the volume sufficient to initiate precipitation.

7. The method of claim 6 wherein the volume is 1.1 to 2 times the volume sufficient to initiate precipitation.

8. The method of claim 1 wherein the volumes of the zinc ions solution is proportional to the anticoagulant concentration in the cryoprecipitate.

9. The method of claim 1 wherein said precipitation is carried out in the presence of heparin.

10. The method of claim 1 which further comprises removing the precipitate from the supernatant, and stabilizing the supernatant against further precipitation by the addition of anticoagulant citrate solution to the supernatant.

11. The method of claim 10 which further comprises extracting fibronectin from the precipitate.

12. The method for the preparation and purification of Factor VIII concentrates which comprises the addition of zinc ions in solution to a material comprising Factor VIII, fibrinogen, and fibronectin, said zinc ions being added in an amount sufficient to initiate a precipitation of fibrinogen and fibronectin rich zinc-protein complexes from said material.

* * * * *